United States Patent
Funkquist

(10) Patent No.: US 11,432,571 B2
(45) Date of Patent: Sep. 6, 2022

(54) METHOD OF HEAT-TREATMENT OF A PRODUCT IN A SEALED CONTAINER OF A PACKAGING MATERIAL

(71) Applicant: Tetra Laval Holdings & Finance S.A., Pully (CH)

(72) Inventor: Ola Funkquist, Lomma (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 282 days.

(21) Appl. No.: 16/620,488

(22) PCT Filed: Jun. 15, 2018

(86) PCT No.: PCT/EP2018/066024
§ 371 (c)(1),
(2) Date: Dec. 7, 2019

(87) PCT Pub. No.: WO2018/234197
PCT Pub. Date: Dec. 27, 2018

(65) Prior Publication Data
US 2020/0138062 A1 May 7, 2020

(30) Foreign Application Priority Data
Jun. 20, 2017 (EP) ..................................... 17176887

(51) Int. Cl.
*A23L 3/015* (2006.01)
*A23L 3/10* (2006.01)
*A23L 5/10* (2016.01)
*B65B 25/00* (2006.01)
(Continued)

(52) U.S. Cl.
CPC .................. *A23L 3/10* (2013.01); *A23L 3/015* (2013.01); *A23L 5/10* (2016.08); *A61L 2/07* (2013.01);
(Continued)

(58) Field of Classification Search
CPC ... A23L 3/10; A23L 3/015; A23L 5/10; A23L 3/02–3/14; B65B 25/001; B65B 55/00;
(Continued)

(56) References Cited

U.S. PATENT DOCUMENTS 3,511,169 A 5/1970 Fritzberg
3,531,300 A * 9/1970 Greenberg ................ A23L 3/10
422/26

(Continued)

FOREIGN PATENT DOCUMENTS

CN 85 1 04 964 A 12/1986
EP 2 145 543 A1 1/2010
(Continued)

OTHER PUBLICATIONS

International Search Report for corresponding Application No. PCT/EP2018/066024, dated Jul. 5, 2018.
(Continued)

*Primary Examiner* — Drew E Becker
(74) *Attorney, Agent, or Firm* — Renner, Otto, Bolsselle & Sklar, LLP

(57) ABSTRACT

A method of heat-treatment of a product in a sealed container of a packaging material is described. The method includes placing the container in a treatment environment having a pressure (P) and a temperature (T), the pressure and the temperature having a ratio (P/T), and adjusting the temperature and/or pressure in the treatment environment to decrease the ratio over a duration in a time period. The time period starts at a time of cooking onset of the product and extends over a time of cooling onset at which time a temperature decrease is started, the time of cooking onset being preceded by a first time period of temperature ramping during which the temperature is increased. An apparatus for
(Continued)

controlling heat-treatment of a product in a sealed container of a packaging material is also described.

8 Claims, 9 Drawing Sheets

(51) Int. Cl.
    *B65B 55/00*     (2006.01)
    *A61L 2/07*     (2006.01)
    *A61L 2/24*     (2006.01)

(52) U.S. Cl.
    CPC .............. *A61L 2/24* (2013.01); *B65B 25/001* (2013.01); *B65B 55/00* (2013.01); *A23V 2002/00* (2013.01); *A61L 2202/14* (2013.01); *A61L 2202/15* (2013.01); *A61L 2202/182* (2013.01)

(58) Field of Classification Search
    CPC . B65B 55/14; A23V 2002/00; A23V 2200/00; A23V 2300/24; A61L 2202/14; A61L 2202/15; A61L 2202/182; A61L 2/24; A61L 2/04–2/07; A61L 2202/181
    USPC ............ 99/359–371; 426/395, 407–409, 412
    See application file for complete search history.

(56) References Cited

U.S. PATENT DOCUMENTS

| | | | | |
|---|---|---|---|---|
| 3,584,569 | A * | 6/1971 | Wieser | A23C 3/027 99/368 |
| 4,874,580 | A * | 10/1989 | Sugisawa | B65B 55/027 422/26 |
| 5,218,829 | A * | 6/1993 | DeJarnette, Jr. | A23L 3/003 62/375 |
| 5,283,033 | A * | 2/1994 | Dodrill | A61L 2/06 426/407 |
| 5,358,030 | A | 10/1994 | Veltman | |
| 9,205,158 | B1 | 12/2015 | Jacob | |
| 2005/0013908 | A1* | 1/2005 | Persoons | A23L 3/10 426/407 |
| 2006/0051235 | A1* | 3/2006 | Christensen | A23L 3/10 422/26 |
| 2009/0071103 | A1 | 3/2009 | Andersson | |
| 2010/0000183 | A1* | 1/2010 | Nantin | B65B 31/04 53/472 |
| 2010/0034938 | A1* | 2/2010 | Stjernberg | A61L 2/07 426/398 |
| 2010/0349380 | | 2/2010 | St Jernberg | |
| 2013/0323367 | A1* | 12/2013 | Pont | A21D 15/06 426/94 |

FOREIGN PATENT DOCUMENTS

| | | |
|---|---|---|
| WO | 98/16431 A1 | 4/1998 |
| WO | 98/52421 A1 | 11/1998 |
| WO | 2004/056666 A1 | 7/2004 |
| WO | 2012/044229 A1 | 4/2012 |

OTHER PUBLICATIONS

Extended European Search Report for corresponding Application No. 17176887.2, dated Nov. 2, 2017.

* cited by examiner

METHOD OF HEAT-TREATMENT OF A PRODUCT IN A SEALED CONTAINER OF A PACKAGING MATERIAL

TECHNICAL FIELD

The present invention generally relates to the field of retort systems for in-container preservation of foodstuffs, and especially to retort systems for use with containers formed from materials having a fiber-based (e.g., paperboard) material component. More particularly, the present invention relates to a method of heat-treatment a product in a sealed container of a packaging material and a related apparatus for controlling heat-treatment of a product in a sealed container of a packaging material.

BACKGROUND

In order to extend the shelf life of a product, it is usual to heat-treat the product and its package. The selected level of heat-treatment depends on the conditions under which the intention is to store the product packed in the package, such as the intended shelf life, and other factors such as the type of food and the initial number of microorganisms in the package. A conventional method of carrying out shelf life-extending heat-treatment of a package and a food product filled into a package is pasteurization or sterilization in a so-called retort device. The packaging container is thus placed in a retort and heated therein with the aid of a circulating medium, e.g. hot steam, and/or water to a temperature which in general lies within the range of 70-130° C., and in some cases up to 150° C. After a predetermined stay time at this selected temperature, the packaging container is typically cooled with a circulating medium, for example cold water. The cooled packaging container is thereafter removed from the retort for further transport and handling. Traditionally, this type of process is usually employed for packages of metal, glass or other materials possessing similar moisture barrier properties. Moreover, these packages are most generally relatively rigid, with the result that, during the retorting process, they are capable of withstanding some inner excess pressure from the product cooking in the closed package. However, in recent times retorting of paper-based packaging laminate has been introduced. A number of variations of packaging laminates have been developed in order to withstand the retorting process. Typically such packaging laminate has a rigid, but foldable core layer of paper or paperboard and outer, liquid-tight coatings of moisture and heat-resistant thermoplastic material on both sides of the core layer. In order to achieve tightness properties also against gases, in particular oxygen gas, the packaging laminate also displays a gas barrier, e.g. an aluminium foil disposed in the laminate. The retortable packaging containers can be produced with the aid of form and seal machines of the type which, from a web or from prefabricated blanks of the packaging material, form, fill and seal finished packages. The filled and sealed, container is thereafter ready for heat-treatment in order to impart to the packed food extended shelf life in the unopened packaging container. However, it has proved that, in certain cases, problems may arise in that the package absorbs liquid, or gas that will condensate to a liquid, during the retorting process to such an extent that its mechanical properties or physical appearance is negatively affected. Such problems may in particular arise at those portions where the packaging laminate displays open edges. The phenomenon may further worsen when such containers are processed in agitation mode.

Hence, an improved method of heat-treatment of a product in a sealed container of a packaging material would be advantageous and in particular allowing for avoiding more of the above-mentioned problems and compromises, including minimizing the water/steam penetration into the packaging material. A related apparatus for controlling heat-treatment of a product in a sealed container of a packaging material would also be advantageous.

SUMMARY

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect a method of heat-treatment of a product in a sealed container of a packaging material is provided. The method comprises placing the container in a treatment environment having a pressure (P) and a temperature (T), the pressure and the temperature having a ratio (P/T), and adjusting the temperature and/or pressure in the treatment environment to decrease said ratio over a duration in a time period, wherein said time period starts at a time of cooking onset of the product and extends over a time of cooling onset at which time a temperature decrease is started, said time of cooking onset being preceded by a first time period of temperature ramping during which said temperature is increased.

According to a second aspect an apparatus for controlling heat-treatment of a product in a sealed container of a packaging material is provided. The container, in use, being positionable in a treatment environment having a pressure (P) and a temperature (T), the pressure and the temperature having a ratio (P/T). The apparatus comprises a control unit configured to adjust the temperature and/or pressure in the treatment environment to decrease said ratio over a duration in a time period, wherein said time period starts at a time of cooking onset of the product and extends over a time of cooling onset at which time a temperature decrease is started, said time of cooking onset being preceded by a first time period of temperature ramping during which said temperature is increased.

Further examples of the invention are defined in the dependent claims, wherein features for the second aspect of the disclosure are as for the first aspect mutatis mutandis.

Some examples of the disclosure provide for an improved retorting of a product in a sealed container of a packaging material.

Some examples of the disclosure provide for a heat-treatment of a product in a sealed container of a packaging material with a reduced penetration of water/steam into the packaging material.

Some examples of the disclosure provide for an improved retorting of a product in a sealed container of a packaging material when the container is agitated.

Some examples of the disclosure provide for increased mechanical integrity of packaging containers being treated in a retort process.

Some examples of the disclosure provide for an improved physical appearance of the packaging containers.

Some examples of the disclosure provide for increasing the variety of packaging materials useable in retort processes.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which.

DETAILED DESCRIPTION

Figure 1:
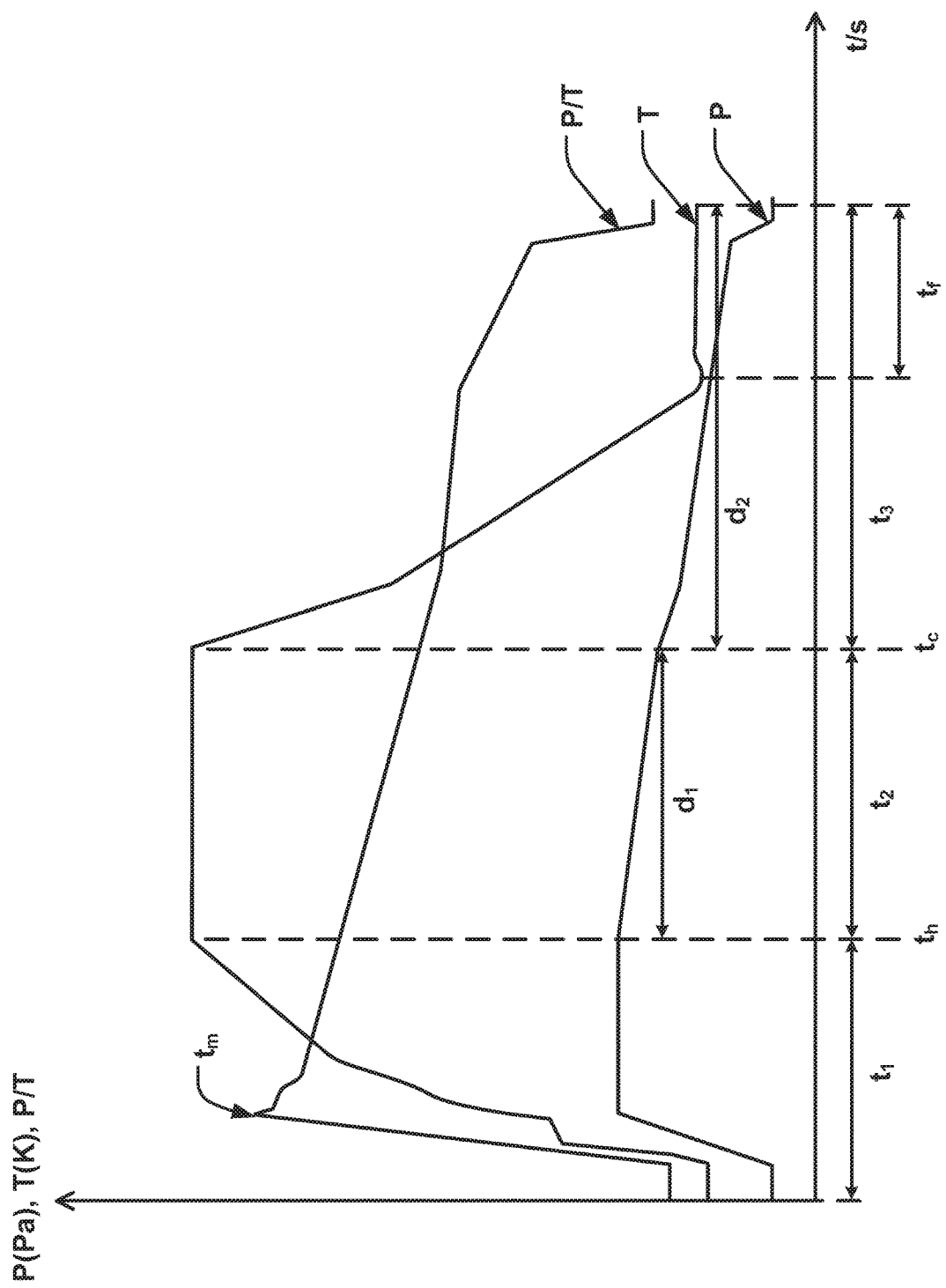
FIG. 1 is a diagram illustrating the temperature (T), pressure (P), and the ratio (P/T) for a period of time (t) in a treatment environment according to one example of the disclosure.

Specific examples of the invention will now be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

Figure 7A:
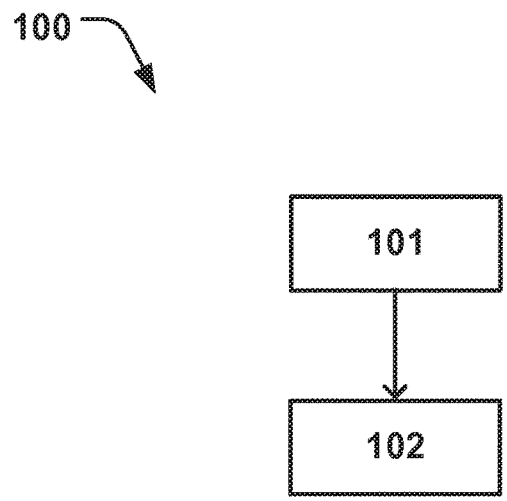
FIGS. 7a-b are flowcharts of a method of heat-treatment of a product in a sealed container of a packaging material according to examples of the disclosure.

FIG. 7a illustrates a flow chart of a method 100 of heat-treatment of a product in a sealed container of a packaging material. The order in which the steps of the method 100 are described and illustrated should not be construed as limiting and it is conceivable that the steps can be performed in varying order.

A method 100 of heat-treatment of a product in a sealed container of a packaging material is thus provided. The method 100 comprises placing 101 the sealed container in a treatment environment having a pressure (P) and a temperature (T). The treatment environment may be provided in a retort device (not shown), i.e. the sealed container may be placed in a retort environment inside the retort device, in which the temperature (T) and pressure (P) may be adjusted. The treatment- or retort environment may thus be a closed or sealed system in which the pressure (P) can be adjusted. The pressure and the temperature has a ratio (P/T), which in the present disclosure is defined as the pressure (P) divided with the temperature (T). The method 100 comprises adjusting 102 the temperature (T) and/or the pressure (P) in the treatment environment to decrease said ratio (P/T) over a duration ($d_1$, $d_2$) in a time period ($t_2$, $t_3$). The aforementioned time period ($t_2$, $t_3$) starts at a time of cooking onset ($t_h$) of the product and extends over a time of cooling onset ($t_c$), i.e. past the time of cooling onset ($t_c$). At the time of cooling onset ($t_c$) a time of temperature decrease is started (i.e. a decrease of the aforementioned temperature (T)). A third time period ($t_3$) of said temperature decrease starts at the time of cooling onset ($t_c$). The time of cooking onset ($t_h$) is preceded by a first time period ($t_1$) of temperature ramping during which the temperature (T) is increased. A second time period ($t_2$) extends between the time of cooking onset ($t_h$) of the product to the time of cooling onset ($t_c$). The duration ($d_1$, $d_2$) may occur in any part of the mentioned time period ($t_2$, $t_3$). By adjusting 102 the temperature (T) and/or the pressure (P) to decrease the ratio (P/T) over a duration ($d_1$, $d_2$) in the time period ($t_2$, $t_3$), the water/steam penetration into the packaging material is reduced. This is due the creation of a molecular driving force being directed from the sealed space of the packaging container towards the retort environment, i.e. the treatment environment. This in turn is due to the increase of the volume of the initial molecules in the void of the sealed packaging container when the ratio (P/T) is decreased. The volume of the void can be considered to be nearly incompressible at the relevant pressure range of the discussed application. The increase in the volume of the molecules will accordingly result in a molecular driving force from the void towards the treatment environment, which will make water penetration into the packaging material more difficult. Thus, by reducing the ratio (P/T) for a duration ($d_1$, $d_2$) occurring in a period from the time of cooking onset ($t_h$) into a time of cooling onset ($t_c$), the water/steam penetration can be reduced during this duration ($d_1$, $d_2$). This is advantageous since the heat treatment starting after the initial temperature ramp, when the target temperature is reached at the time of cooking onset ($t_h$), is typically associated with a temperature- or pressure plateau in previous methods. Such plateau will however result in that there is no molecular driving force, or a very limited driving force, that can act to prevent the water/steam penetration into the packaging material. There will be no margin for fluctuations in the pressure or temperature, which often is the case, and the risk of a molecular driving force that is directed from the treatment environment into the void in the packaging container, is increased, which will increase the water/steam penetration into the packaging material.

Figure 2:
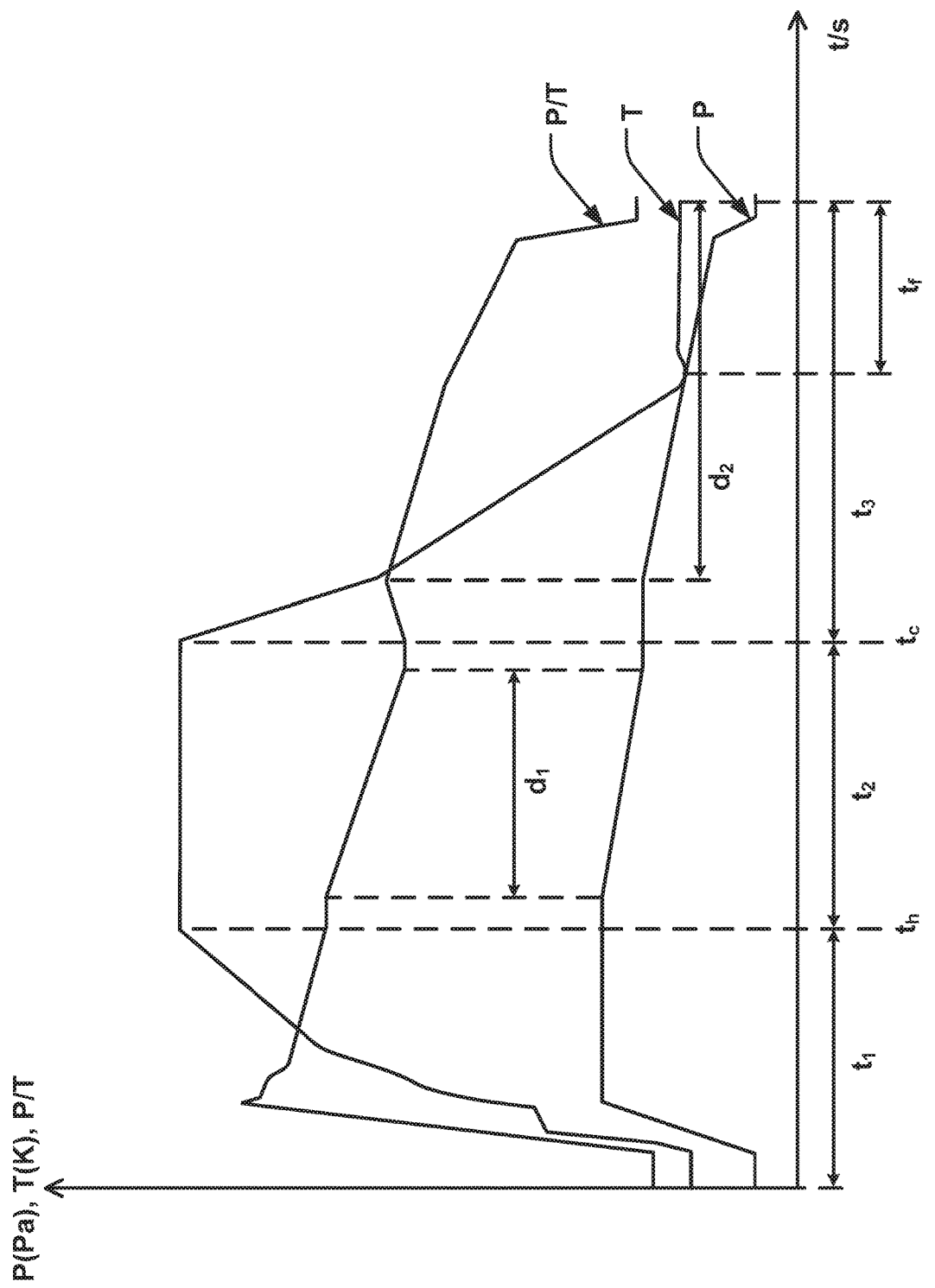
FIG. 2 is a diagram illustrating the temperature (T), pressure (P), and the ratio (P/T) for a period of time (t) in a treatment environment according to one example of the disclosure.
Figure 6:
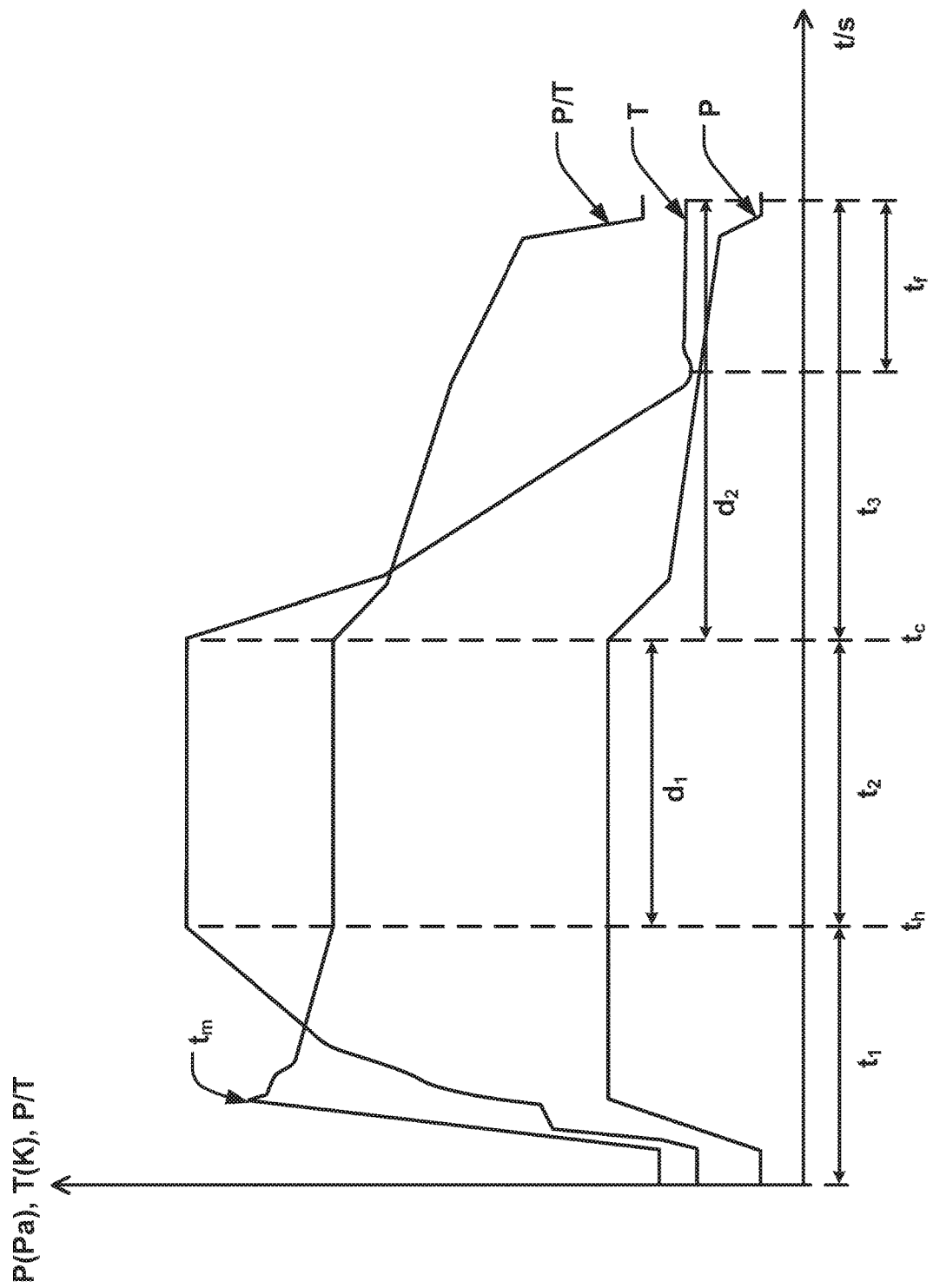
FIG. 6 is a diagram illustrating the temperature (T), pressure (P), and the ratio (P/T) for a period of time (t) in a treatment environment according to one example of the disclosure.

FIG. 1 is a schematic diagram of a heat-treatment process in which the ratio (P/T) is reduced over a duration ($d_1$, $d_2$) that occurs in a time period that extends from the time of cooking onset ($t_h$) and past the time of cooling onset ($t_c$). As mentioned, the duration ($d_1$, $d_2$) of ratio (P/T) decrease may occur in any part of the mentioned time period ($t_2$, $t_3$), i.e. in $t_2$ or in $t_3$, or in both $t_2$ and $t_3$. FIG. 6 illustrates another example where the duration of ratio (P/T) decrease is represented by a duration ($d_2$) occurring from the time of cooling onset ($t_c$), i.e. in the third time period ($t_3$). In the latter case, the duration refers only to $d_2$. As further discussed below, the length of the duration ($d_1$, $d_2$) within the time period (from $t_2$ to $t_3$) may vary, as schematically illustrated in FIG. 2. I.e. the ratio (P/T) may be decreased over a duration which is shorter than the time period.

Figure 3:
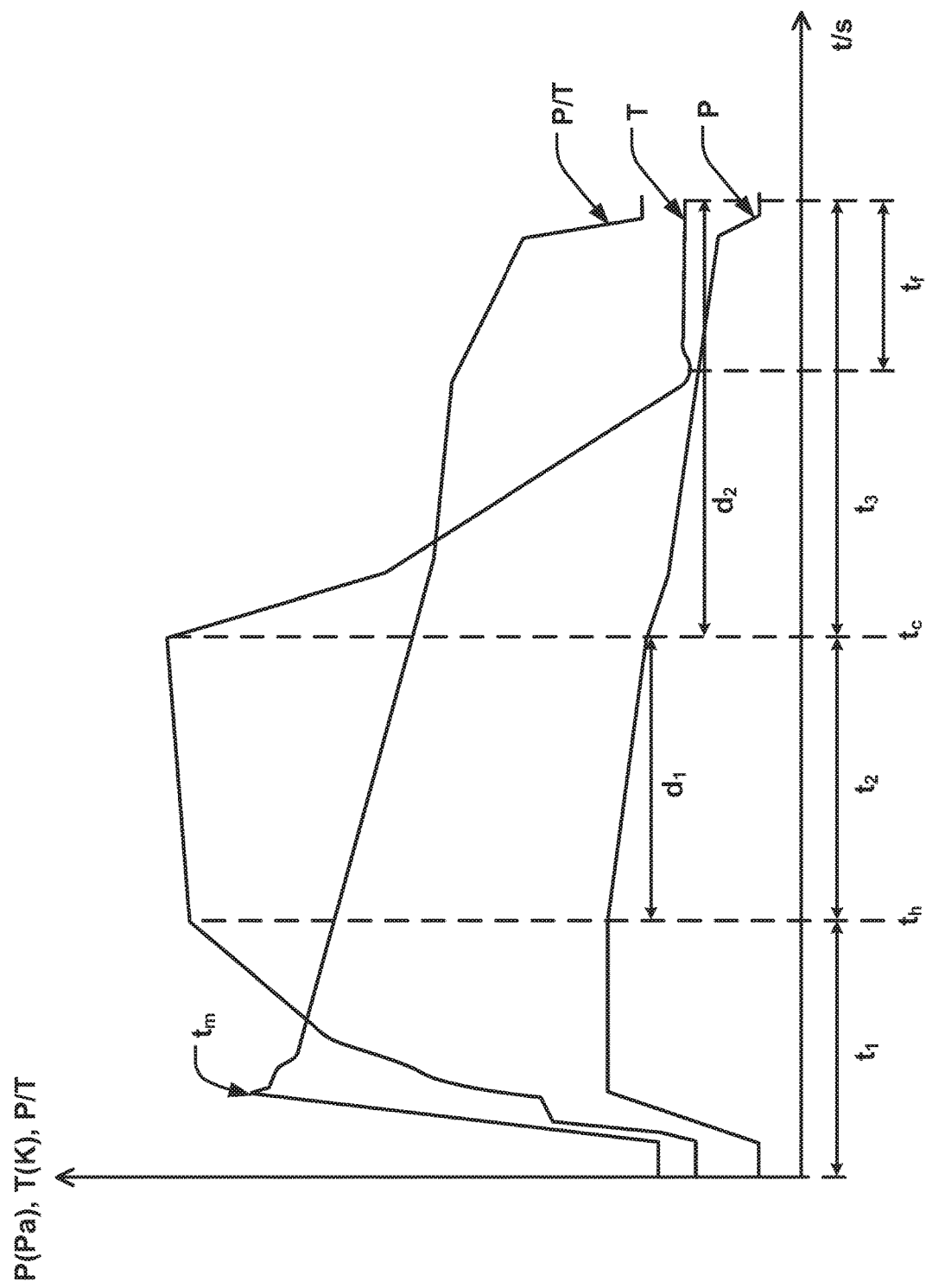
FIG. 3 is a diagram illustrating the temperature (T), pressure (P), and the ratio (P/T) for a period of time (t) in a treatment environment according to one example of the disclosure.
Figure 4:
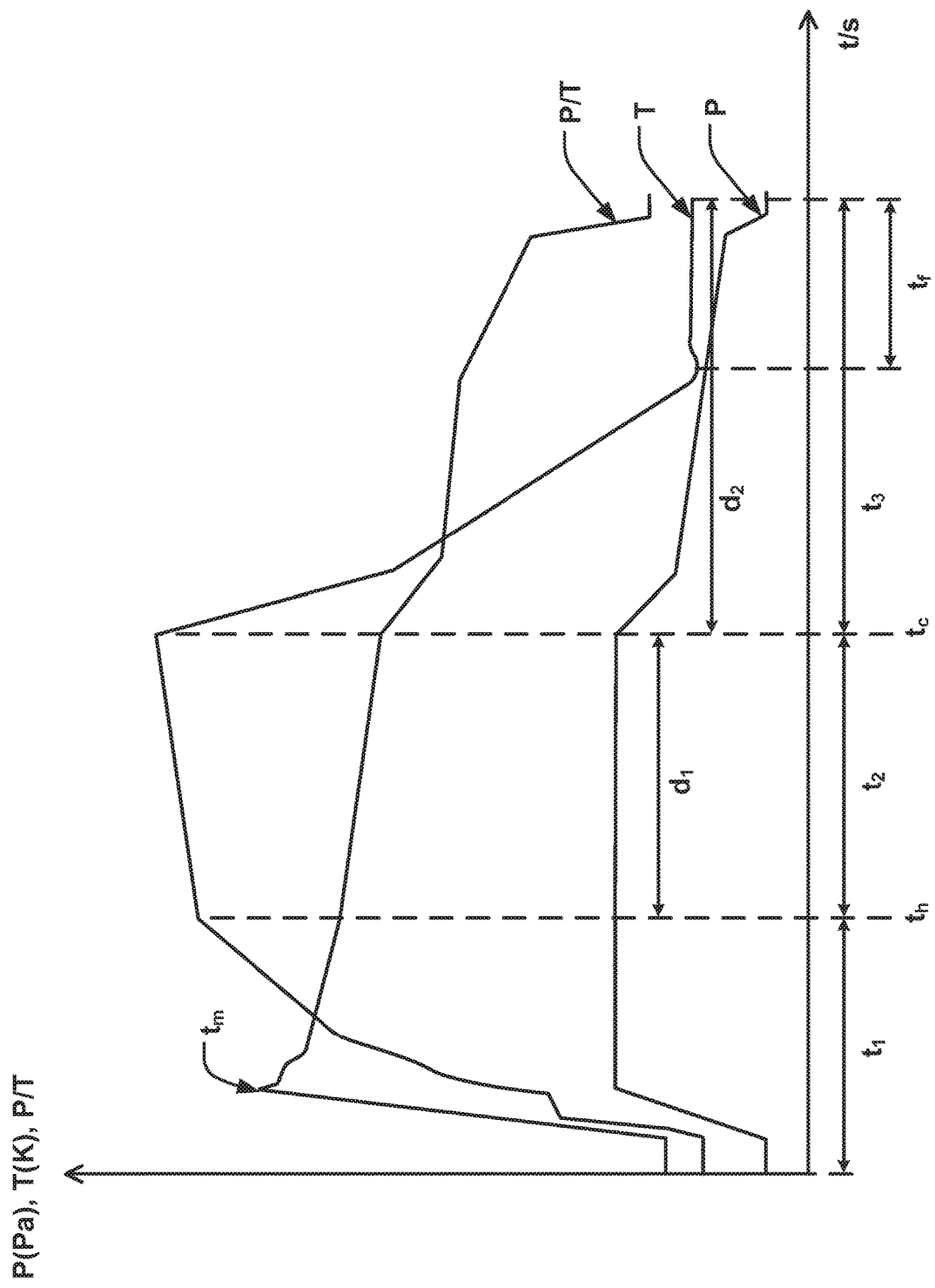
FIG. 4 is a diagram illustrating the temperature (T), pressure (P), and the ratio (P/T) for a period of time (t) in a treatment environment according to one example of the disclosure.
Figure 5:
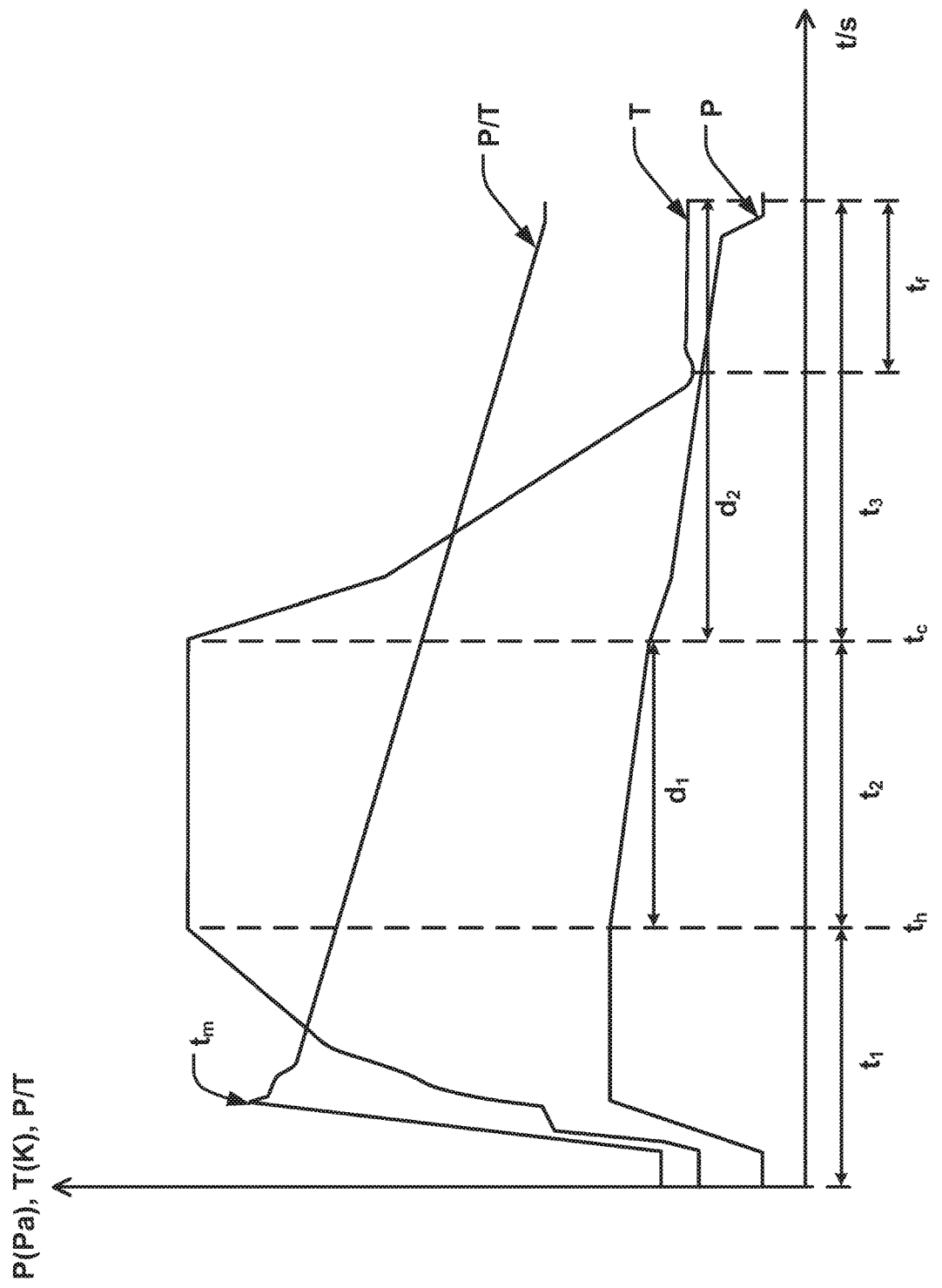
FIG. 5 is a diagram illustrating the temperature (T), pressure (P), and the ratio (P/T) for a period of time (t) in a treatment environment according to one example of the disclosure.

Returning again to FIG. 1, in this example, the ratio (P/T) is lowered over a first duration ($d_1$) and a second duration ($d_2$) occurring in respective second and third time periods ($t_2$, $t_3$). More particularly, the pressure (P) is lowered over the both the first and second durations ($d_1$, $d_2$) to provide for the decrease in the ratio (P/T). Alternatively or in addition, it is conceivable that the temperature (T) may be gradually increased over the first duration ($d_1$) to contribute to lowering the ratio (P/T), as illustrated in FIG. 3. Further, FIG. 4 illustrates another example where the pressure (P) is kept substantially constant during the first duration ($d_1$), and the temperature (T) is gradually increased, even after the initial period of temperature ramping ($t_1$), to provide for the decrease of the ratio (P/T) from the time of cooking onset ($t_h$). As mentioned, it is conceivable that the first duration ($d_1$) may vary in length, as schematically illustrated in FIG. 2. Thus, the ratio (P/T) may be lowered during part of the second time period ($t_2$).

Regardless, the method 100 provides for an improved heat-treatment of a sealed packaging container, with reduced penetration of water or steam into the packaging material. Accordingly, the mechanical integrity of the packaging container does not need to be compromised and it is possible to use a wide variety of packaging materials in the retort process without risking any degradation thereof. Although reference is made to water and steam above, it is conceivable that the penetration of any other heating or cooling medium into the packaging material, when injected into the treatment environment, can be minimized with the method 100 described above due to the molecular driving force provided. The method 100 is advantageous both for a static process or a process when the package is exposed to some kind of agitation i.e. gentle motion or rotation. The method 100 may be particularly advantageous and important during agitation since the package is exposed to more mechanical stress in comparison with a static process.

Figure 7B:
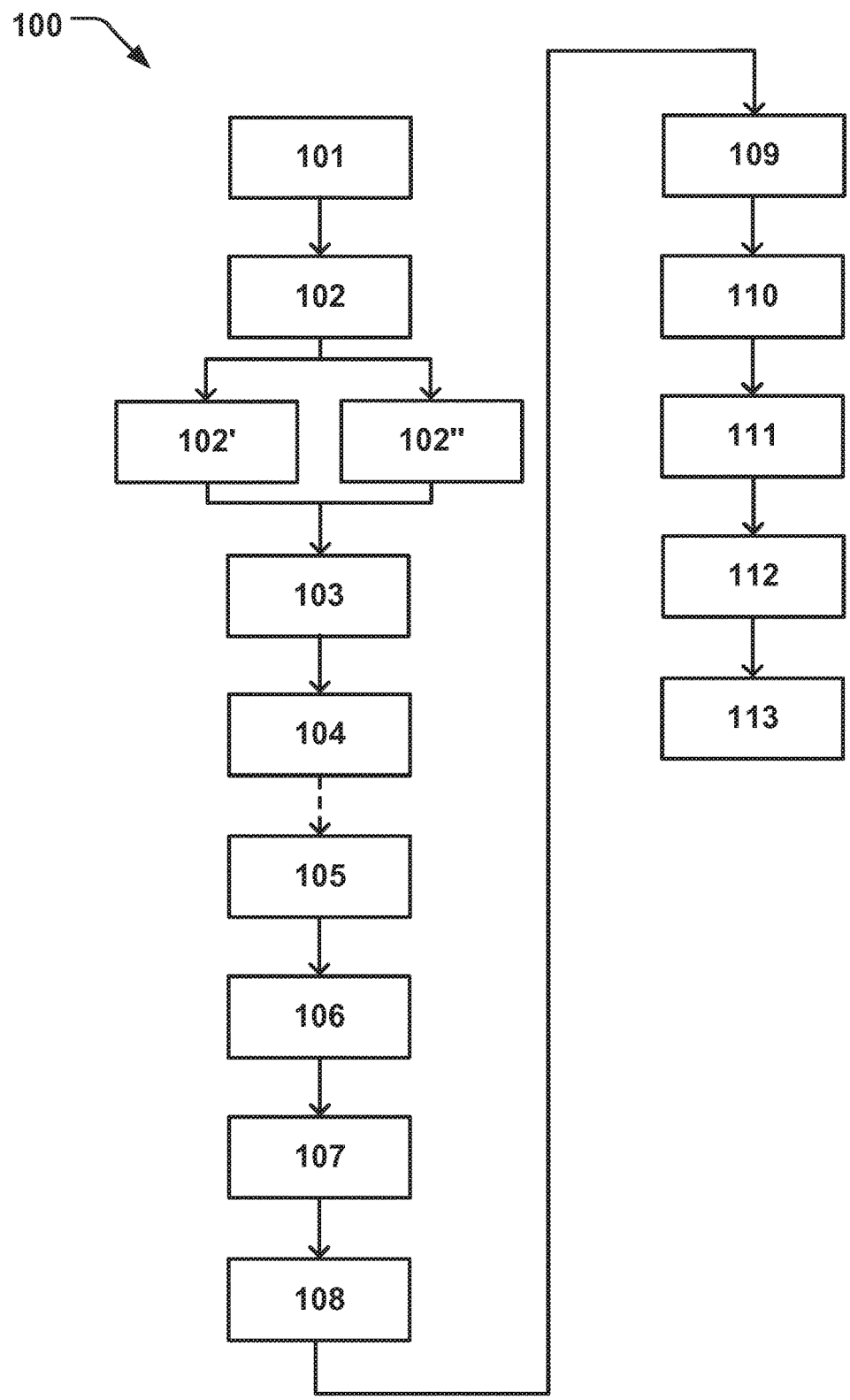

FIG. 7b illustrates a further flow chart of a method 100 of heat-treatment of a product in a sealed container of a packaging material. The order in which the steps of the method 100 are described and illustrated should not be construed as limiting and it is conceivable that the steps can be performed in varying order.

As described above, the mentioned time period ($t_2$, $t_3$) may comprise a second ($t_2$) and a third ($t_3$) time period, and the method 100 may comprise adjusting 102' the temperature (T) and/or pressure (P) to decrease the ratio (P/T) over the first duration ($d_1$) in at least the second time period ($t_2$) extending from the time of cooking onset ($t_h$) of the product to the time of cooling onset ($t_c$) at which time the third time period ($t_3$) of temperature decrease is started, as illustrated in e.g. FIGS. 1-5. Further, the method 100 may alternatively or in addition comprise adjusting 102'' the temperature (T) and/or pressure (P) to decrease said ratio (P/T) over a second duration ($d_2$) in the third time period ($t_3$) starting at the time of cooling onset ($t_c$), as illustrated in FIG. 6.

As mentioned, decreasing said ratio (P/T) may comprise lowering 103 the pressure. This may be particularly advantageous in some situations, where it is desired to provide for a molecular driving force being directed from the void towards the treatment environment without needing to increase the temperature further after the time of cooking onset ($t_h$), which may be detrimental to some products. The method 100 may comprise continuously decreasing the pressure (P), i.e. without interruptions in the decrease, in order to provide for a substantially sustained molecular driving force from the void towards the treatment environment, and thereby further reduce the amount of penetration of water or steam into the packaging material in an uninterrupted manner.

An apparatus 200 for controlling heat-treatment of a product in a sealed container of a packaging material is provided. As mentioned, during use, the container is being provided in a treatment environment having a pressure (P) and a temperature (T). The container can thus be placed in the treatment environment, i.e. the container is positionable in the treatment environment. The pressure (P) and the temperature (T) has a ratio (P/T) by which the pressure (P) is divided with the temperature (T). The apparatus 200 comprises a control unit 201, being schematically illustrated in FIG. 8, and being configured to adjust 102 the temperature (T) and/or pressure (P) to decrease said ratio (P/T) over a duration ($d_1$, $d_2$) occurring in a time period ($t_2$, $t_3$), wherein the aforementioned time period ($t_2$, $t_3$) starts from a time of cooking onset ($t_h$) of the product and extends over (i.e. past) a time of cooling onset ($t_c$) at which time a time period of temperature decrease is started. The time of cooking onset ($t_h$) being preceded by a first time period ($t_1$) of temperature ramping during which said temperature (T) is increased. The apparatus 200 thus provides for the advantageous benefits as described above for the method 100 and in relation to FIGS. 1-5. The apparatus 200 and the control unit 201 may be connected to a retort device (not shown), so that the control unit 200 can adjust the temperature (T) and/or pressure (P) in the treatment environment inside the retort device. A retort device, to which the apparatus 200 and control unit 201 is connected is thus also provided in an aspect of the present disclosure.

The control unit 201 may be configured to lower the pressure (P) to provide the decrease of said ratio (P/T), as described above.

Figure 8:
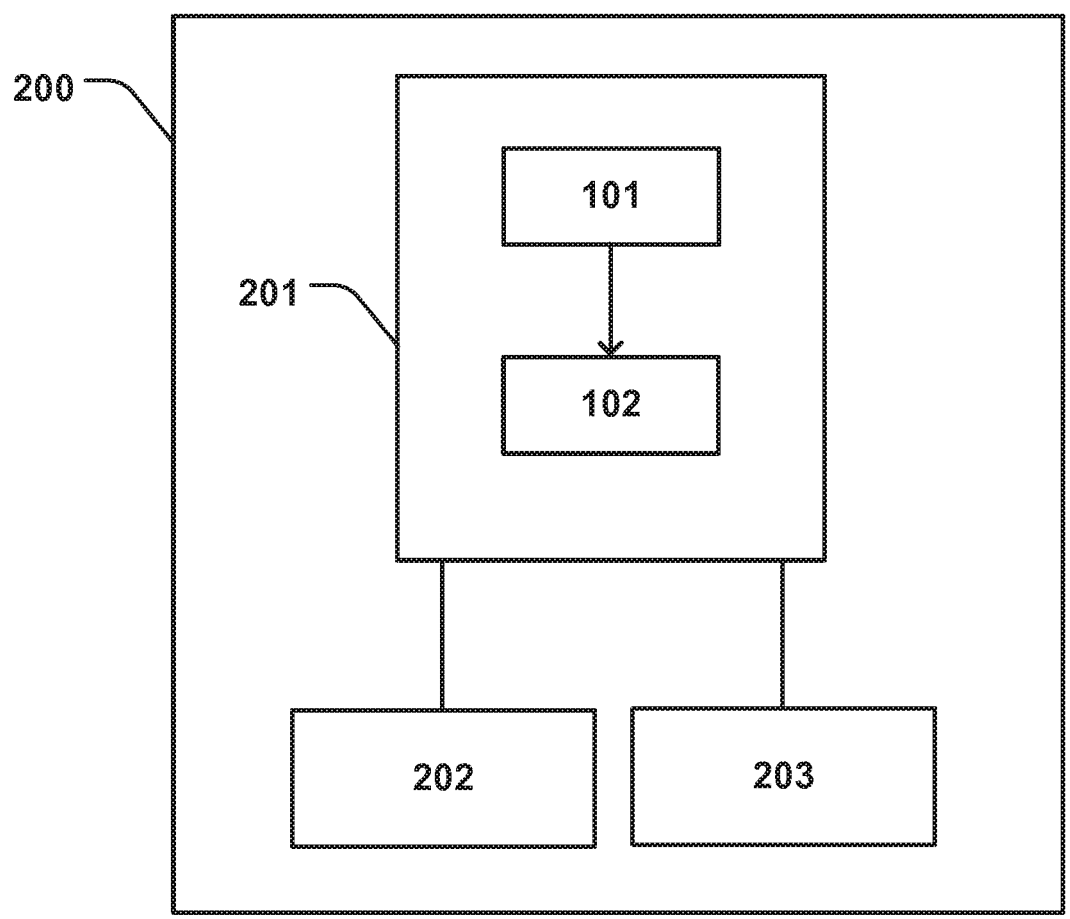
FIG. 8 is a schematic illustration of an apparatus for controlling heat-treatment of a product in a sealed container of a packaging material according to one example of the disclosure.

The apparatus 200 may comprise a pressure sensor 202 configured to determine the pressure (P), and a temperature sensor 203 configured to determine the temperature (T), as schematically illustrated in FIG. 8. The pressure sensor 202 and temperature sensor 203 are configured to communicate respective sensor data containing the pressure (P) and the temperature (T) to the control unit 201. The control unit 201 may furthermore be configured to decrease the pressure (P) and/or increase the temperature (T) in response to the sensor data to maintain a continuous decrease of the ratio (P/T) during the heat-treatment, at least after a heating medium being supplied to the treatment environment. The control unit 201 thus being able to efficiently provide for a sustained molecular driving force from the void of the packaging container to the treatment environment, and preventing penetration of the heating medium (and/or cooling medium) into the packaging material for a wide range of temperature and pressures. For example, the control unit 201 may sense that the temperature (T) is levelling out, e.g. in the second time period ($t_2$), and may start to decrease the pressure (P) at a determined rate to maintain a decrease of the ratio (PIT). The control unit 201 may sense that the speed by which the temperature (T) is reduced is increased, and start to increase the speed of pressure (P) decrease to maintain a lowering of the ratio (P/T) even when the temperature is decreased. The temperature (T) and pressure may have respective threshold ranges programmed into the control unit 201 so that the ratio (P/T) can be continuously decreased, via either temperature or pressure adjustments while staying within the respective thresholds.

The method 100 may comprise decreasing 104 the ratio (P/T) over a second duration ($d_2$) in the third time ($t_3$) period by lowering the pressure (P) and/or increasing the temperature (T). FIG. 1 illustrates an example where the pressure (P) is lowered after the time of cooling onset ($t_c$), i.e. in the third time period ($t_3$). This provides for maintaining a decrease in the ratio (P/T) even when the temperature (T) is lowered in the cooling phase of the product. A molecular driving force directed from the void towards the treatment environment can thus be sustained even during the cooling phase, which provides for further reduction of the penetration of medium into the packaging material. As with the first duration ($d_1$), the second duration ($d_2$) may vary in length in the third time period ($t_3$) to optimize the process. It may be advantageous to maintain the pressure decrease for the substantially the whole duration of the cooling phase.

The ratio (P/T) may be continuously decreased 105 over the second ($t_2$) and third ($t_3$) time periods. The time of the first and second durations ($d_1$, $d_2$) of decreasing the ratio (P/T) may thus correspond substantially to the time of the first and second time periods ($t_2$, $t_3$). As elucidated above, such continuous decrease, achieved for example by lowering the pressure (P), may provide for a sustained molecular driving force over such extended period and reduced penetration of water and steam into the packaging material.

The ratio (P/T) may be decreased 106 in the third time period ($t_3$) until the product reach a temperature substantially correspond to a final temperature of the product after the heat treatment, for example somewhat above room temperature such as 40° C. Such extended decrease of the ratio (P/T) until the product has cooled to room temperature can provide for further minimizing water penetration into the packaging material, or as mentioned above, reduced penetration of any other medium that may be introduced into the treatment environment.

The temperature (T) of the treatment environment may be kept substantially constant in a final segment ($t_f$) of the third time period while the pressure (P) is lowered 107. This is illustrated in e.g. FIG. 1. The ratio (P/T) thus continues to decrease in the final segment ($t_f$). The pressure (P) may be lowered until the treatment environment has been evacuated of the cooling medium, so that the molecular driving force is directed from the void towards the surrounding space of the treatment environment until there is no risk of penetration of the medium into the packaging material.

The method 100 may comprise keeping the temperature (T) of the treatment environment substantially constant from the time of cooking onset ($t_h$) to the time of cooling onset ($t_c$) while decreasing 108 the ratio (P/T) by lowering the pressure at least between the time of cooking onset ($t_h$) to the time of cooling onset ($t_c$). This provides for reducing the ratio (P/T) while keeping the temperature at a desired level adapted to the particular heat-treatment process.

The pressure (P) may be lowered with an increased rate 109 in the third time period ($t_3$) compared to the second time period ($t_2$) to maintain a decrease of the ratio (P/T) in the third time period ($t_3$) in which the temperature (T) is decreased. Thus, it is possible to maintain a molecular driving force directed from the void to the treatment environment even during the cooling of the product in the third time period ($t_3$).

The method 100 may comprise delivering 110 a heating medium containing a fluid or gas to the packaging container in the treatment environment, i.e. exposing the packaging container to the heating medium, to provide the heat-treatment, and increasing 111 the ratio (P/T) before delivering the heating medium to the packaging container at a time of fluid or gas onset ($t_m$). The gas may for example be steam. The heating medium can be delivered via a pump in case of having a fluid or via a fan in case of having a gas such as steam as heating medium. This is illustrated in e.g. FIG. 1, where the ratio (P/T) is increased until time ($t_m$), as the treatment environment is pressurized. Once the treatment environment has been pressurized to a target pressure, the packaging container can be exposed to the heating medium while the lowering of the ratio (P/T) is initiated. The molecular driving force may thus prevent penetration of the heating medium into the packaging material already from start, when the packaging container is exposed to the heating medium.

Then the ratio (P/T) may be continuously decreased 112 from the time of fluid or gas onset ($t_m$) until the product reach a final temperature after the heat-treatment by lowering the pressure and/or increasing the temperature, in order to provide for a minimized penetration of the medium into the packaging material as elucidated above. As further exemplified in FIG. 5, it is conceivable that the derivative of the ratio (P/T) decrease is substantially constant over the second ($t_2$) and third ($t_3$) time periods, and possibly also over the final segment ($t_f$). The temperature and pressure may thus be adjusted accordingly to provide for such constant rate of decrease of the ratio, which may be particularly advantageous in some situations and applications.

The pressure (P) may be lowered or kept substantially constant during the first time period ($t_1$) after the time of fluid or gas onset. It is still possible to maintain a decrease of the ratio (P/T) in the first period ($t_1$) when the temperature (T) of the heating medium is increased.

The packaging container encloses a volume occupied by a void and the product. The void contains a substance having an initial volume before the heat-treatment. The method 100 may comprise increasing 113 the initial volume during the heat-treatment by decreasing the ratio (P/T) by lowering the pressure (P) and/or increasing the temperature (T).

The present invention has been described above with reference to specific examples. However, other examples than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A method of heat-treatment of a product in a sealed container of a paper-based packaging laminate enclosing a volume occupied by a void and the product, the method comprising:
   placing the sealed container enclosing the product in a treatment environment being a retort environment in a retort device having a pressure (P) and a temperature (T), wherein the pressure and the temperature has a ratio (P/T),
   adjusting the temperature and/or pressure in the treatment environment to decrease said ratio over a duration ($d_1$, $d_2$) in a time period ($t_2$, $t_3$) to maintain a molecular driving force directed from the void to the treatment environment, wherein said time period starts at a time of cooking onset ($t_h$) of the product and extends over a time of cooling onset ($t_c$) at which time a temperature decrease is started, said time of cooking onset being preceded by a first time period ($t_1$) of temperature ramping during which said temperature is increased, wherein the time period comprises a second ($t_2$) and a third ($t_3$) time period, wherein the method comprises adjusting to decrease said ratio over a first duration ($d_1$) in at least the second time period ($t_2$) extending from the time of cooking onset ($t_h$) of the product to the time of cooling onset ($t_c$) at which time the third time period ($t_3$) of temperature decrease is started, by keeping the temperature of the treatment environment constant, while decreasing said ratio by continuously lowering the pressure, from the time of cooking onset to the time of cooling onset, wherein the method further comprises adjusting to decrease said ratio over a second duration ($d_2$) in the third time period ($t_3$) starting at the time of cooling onset ($t_c$), wherein said ratio is continuously decreased over the second and third time periods, whereby the time of the first and second duration of decreasing said ratio corresponds to the time of the second and third time periods, and wherein said ratio is decreased in the third time period.

2. The method according to claim 1, wherein the temperature of the treatment environment is kept substantially constant in a final segment ($t_f$) of the third time period while the pressure is lowered.

3. The method according to claim 1, wherein the pressure is lowered with an increased rate in the third time period compared to the second time period to maintain a decrease of said ratio in the third time period in which the temperature is decreased.

4. The method according to claim 1, comprising:
delivering a heating medium containing a fluid or gas to the packaging container in the treatment environment to provide said heat-treatment,
increasing said ratio before delivering the heating medium to the packaging container at a time of fluid or gas onset ($t_m$).

5. The method according to claim 4, wherein said ratio is continuously decreased from the time of fluid or gas onset until the product reach a final temperature after the heat-treatment by lowering the pressure and/or increasing the temperature.

6. The method according to claim 4, wherein the pressure is lowered or kept substantially constant during the first time period after the time of fluid or gas onset.

7. The method according to claim 1, wherein the void contains a substance having an initial volume before the heat-treatment, the method comprising increasing the initial volume during the heat-treatment by decreasing said ratio by lowering the pressure and/or increasing the temperature.

8. An apparatus for controlling heat-treatment of a product in a sealed container of a paper-based packaging laminate enclosing a volume occupied by a void and the product, the sealed container enclosing the product, in use, being positionable in a treatment environment having a pressure (P) and a temperature (T), wherein the pressure and the temperature has a ratio (P/T), the apparatus comprising:

a control unit configured to adjust the temperature and/or pressure in the treatment environment to decrease said ratio over a duration ($d_1$, $d_2$) in a time period ($t_2$, $t_3$) to maintain a molecular driving force directed from the void to the treatment environment, wherein said time period starts at a time of cooking onset ($t_h$) of the product and extends over a time of cooling onset ($t_c$) at which time a temperature decrease is started, said time of cooking onset being preceded by a first time period ($t_1$) of temperature ramping during which said temperature is increased, the time period comprises a second ($t_2$) and a third ($t_3$) time period, wherein the method comprises adjusting to decrease said ratio over a first duration ($d_1$) in at least the second time period ($t_2$) extending from the time of cooking onset ($t_h$) of the product to the time of cooling onset ($t_c$) at which time the third time period ($t_3$) of temperature decrease is started, by keeping the temperature of the treatment environment constant, while decreasing said ratio by continuously lowering the pressure, from the time of cooking onset to the time of cooling onset, the apparatus comprising a pressure sensor configured to determine said pressure, a temperature sensor configured to determine said temperature, the pressure sensor and temperature sensor being configured to communicate respective sensor data containing said pressure and said temperature to the control unit, wherein the control unit is configured to continuously decrease the pressure in response to the sensor data to maintain a continuous decrease of said ratio during the heat-treatment, at least after a heating medium being delivered to the packaging container, wherein the temperature of the treatment environment is kept constant in a final segment ($t_f$) of the third time period while the pressure is lowered, the pressure is lowered with an increased rate in the third time period compared to the second time period to maintain a decrease of said ratio in the third time period in which the temperature is decreased, the pressure is lowered or kept substantially constant during the first time period after the time of fluid or gas onset, and the control unit is configured to lower the pressure to provide the decrease of said ratio.

* * * * *